US006270785B1

(12) United States Patent
Selisko et al.

(10) Patent No.: US 6,270,785 B1
(45) Date of Patent: Aug. 7, 2001

(54) PRIMARY SEQUENCE AND CDNA OF INSECTICIDALLY EFFECTIVE TOXINS FROM SCORPIONS OF THE GENUS CENTRUROIDES

(75) Inventors: Barbara Selisko; Consuelo Garcia-Rodriguez; Angelina Ramirez-Navarro; Fernando Zamudio-Zuñiga; Baltazar Becerril-Lujan; Lourival D. Possani-Postay, all of Morelos (MX)

(73) Assignee: Universidad Nacional Autonoma de Mexico (MX)

( * ) Notice: Subject to any disclaimer, the term of this patent is extended or adjusted under 35 U.S.C. 154(b) by 0 days.

(21) Appl. No.: 09/053,021

(22) Filed: Apr. 1, 1998

Related U.S. Application Data (63) Continuation-in-part of application No. 08/848,261, filed on Apr. 29, 1997, now abandoned.
(60) Provisional application No. 60/017,007, filed on Apr. 30, 1996.

(51) Int. Cl.[7] .................................................. A01N 25/00
(52) U.S. Cl. ............................ 424/405; 530/324; 530/350
(58) Field of Search .................................. 530/324, 350; 424/405

(56) References Cited

U.S. PATENT DOCUMENTS

| | | |
|---|---|---|
| 4,797,279 | 1/1989 | Karamata et al. . |
| 5,177,308 | 1/1993 | Barton et al. . |
| 5,441,934 | 8/1995 | Krapcho et al. . |

OTHER PUBLICATIONS

Possani et al., The Amino Terminal Sequence of Several Toxins from the Venom of the Mexican Scorpion Centruroides Noxius Hoffman. Carlsberg Res. Commun. 46:207–214, 1981.*

Alagon et al., Isolation and Characterization of Two Toxins from the Mexican Scorpion Centruroides Limpidus Limpidus Karsch. Comp. Biochem. Physiol. 89B:153–161, 1988.*

Stewart; Lorna M. et al., "Construction Of An Improved Baculovirus Insecticide Containing An Insect–Specific Toxin Gene", *Nature*, vol. 352, pp. 85–88 (Jul. 1991).

Hammock; Bruce D. et al., "Expression And Effects OF The Juvenile Hormone Esterase In A Baculovirus Vector", *Nature*, vol. 344, pp. 458–461 (Mar. 1990).

Hilder; Vaughan A. et al., "A Novel Mechanism Of Insect Resistance Engineered Into Tobacco", *Nature*, vol. 330, pp. 160–163 (Nov. 1987).

Becerril; Baltazar et al., "Cloning and Characterization of cDNAs That Code For Na+–Channel–Blocking Toxins Of The Scorpion *Centruroides Noxius* Hoffman", *Gene*, vol. 128. pp. 165–171 (1993).

* cited by examiner

*Primary Examiner*—Donna C. Wortman
(74) *Attorney, Agent, or Firm*—Finnegan, Henderson, Farabow, Garrett & Dunner

(57) ABSTRACT

This invention provides insecticidally effective toxins isolated from the venom of the Mexican scorpions of the genus Centruroides and the cDNA encoding one of the toxins.

11 Claims, 3 Drawing Sheets

```
        1         5          10        15        20        25        30        35        40        45        50        55        60        65
Cn10    -KEGYLVNKSTGCKYNCLILGENKNCDMECKAKNQGGSYGYCYKLACWCEGLPESTPTYPIPGKTCRTK
         ||||||||| |||||||||||| |||  |||||  ||  ||||||||||||||| |||||||| |||
C113    KKDGYLVNKYTGCKVNCYKLGENKFCNRECRAKHRGGDYGYCYGFGCYCEGLADSTETWPLSNKRCG--
```

FIG. 1

```
SIGNAL PEPTIDE
      -10                                              -5                                                     TOXIN
                                                                                                              1                          5                          10
ATC ACT GCT TGT TTG GTC CTG ATC GGA ACA GTG TGC GCA AAG GAA GGT TAT CTG GTG AAC AAG AGC ACA GGC
 I   T   A   C   L   V   L   I   G   T   V   C   A   K   E   G   Y   L   V   N   K   S   T   G
          15                  20                  25                  30                  35
TGT AAA TAC AAC TGC TTG ATA TTG GGA GAA AAC AAA AAC TGT GAT ATG GAA TGC AAA GCG AAG AAC CAA GGA
 C   K   Y   N   C   L   I   L   G   E   N   K   N   C   D   M   E   C   K   A   K   N   Q   G
              40                  45                  50                  55
GGT AGT TAC GGC TAT TGC TAC AAG CTT GCA TGC TGG TGC GAA GGT TTG CCC GAA AGT ACA CCG ACT TAT CCC
 G   S   Y   G   Y   C   Y   K   L   A   C   W   C   E   G   L   P   E   S   T   P   T   Y   P
50                 65                         NON-CODING END
ATT CCT GGT AAA ACA TGC AGA ACA AAA TAA TGGCAACATCTTTTTATTGTCACACAACAGAAATATTGTAACGCTTCTTAATTGC
 I   P   G   K   T   C   R   T   K  STOP
AATTAAACAAAATAAAATGTAATACCTTCAAAAAAAAAAAAAAA
```

FIG. 2

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 68 amino acids
      (B) TYPE: amino acid
      (C) STRANDEDNESS: single
      (D) TOPOLOGY: linear    (ii) MOLECULE TYPE: peptide    (vi) ORIGINAL SOURCE:
      (A) ORGANISM: Centruroides noxius Hoffman
      (D) DEVELOPMENTAL STAGE: Adult
      (F) TISSUE TYPE: venom    (x) PUBLICATION INFORMATION:
      (A) AUTHORS: Selisko, Barbara
          Garcia, Consuelo
          Becerril, Baltazar
          Delepierre, Muriel
          Possani, Lourival D.
      (B) TITLE: An insect-specific toxin from Centruroides
          noxius Hoffman cDNA, primary structure,
          three-dimensional model and electrostatic surface potentials in comparison with other toxin variants
        (C) JOURNAL: Eur. J. Biochem.
        (D) VOLUME: 242
        (F) PAGES: 235-242
        (G) DATE: 1996
        (K) RELEVANT RESIDUES IN SEQ ID NO:1: FROM 1 TO 68

(xi) SEQUENCE DESCRIPTION: SEQ ID NO:1:

Lys Glu Gly Tyr Leu Val Asn Lys Ser Thr Gly Cys Lys Tyr Asn Cys
1               5                   10                  15

Leu Ile Leu Gly Glu Asn Lys Asn Cys Asp Met Glu Cys Lys Ala Lys
                20                  25                  30

Asn Gln Gly Gly Ser Tyr Gly Tyr Cys Tyr Lys Leu Ala Cys Trp Cys
            35                  40                  45

Glu Gly Leu Pro Glu Ser Thr Pro Thr Tyr Pro Ile Pro Gly Lys Thr
    50                  55                  60

Cys Arg Thr Lys
65

(2) INFORMATION FOR SEQ ID NO:2:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Centruroides limpidus limpidus Karsch
        (D) DEVELOPMENTAL STAGE: Adult
        (F) TISSUE TYPE: venom (xi) SEQUENCE DESCRIPTION: SEQ ID NO:2:

Lys Lys Asp Gly Tyr Leu Val Asn Lys Tyr Thr Gly Cys Lys Val Asn
1               5                   10                  15

Cys Tyr Lys Leu Gly Glu Asn Lys Phe Cys Asn Arg Glu Cys Arg Ala
                20                  25                  30

Lys His Arg Gly Gly Asp Tyr Gly Tyr Cys Tyr Gly Phe Gly Cys Tyr
            35                  40                  45

Cys Glu Gly Leu Ala Asp Ser Thr Glu Thr Trp Pro Leu Ser Asn Lys
    50                  55                  60

Arg Cys Gly
65

(2) INFORMATION FOR SEQ ID NO:3:

(i) SEQUENCE CHARACTERISTICS:
        (A) LENGTH: 301 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Centruroides noxius Hoffman
        (D) DEVELOPMENTAL STAGE: Adult (vii) IMMEDIATE SOURCE:
        (A) LIBRARY: cDNA
        (B) CLONE: CngtVIII (ix) FEATURE:
        (A) NAME/KEY: sig_peptide
        (B) LOCATION: 1..39

(ix) FEATURE:
    (A) NAME/KEY: CDS
    (B) LOCATION: 1..243

(ix) FEATURE:
    (A) NAME/KEY: mat_peptide
    (B) LOCATION: 40..243

(xi) SEQUENCE DESCRIPTION: SEQ ID NO:3:

```
ATC ACT GCT TGT TTG GTC CTG ATC GGA ACA GTG TGC GCA AAG GAA GGT      48
Ile Thr Ala Cys Leu Val Leu Ile Gly Thr Val Cys Ala Lys Glu Gly
-13         -10              -5                   1

TAT CTG GTG AAC AAG AGC ACA GGC TGT AAA TAC AAC TGC TTG ATA TTG      96
Tyr Leu Val Asn Lys Ser Thr Gly Cys Lys Tyr Asn Cys Leu Ile Leu
        5               10                  15

GGA GAA AAC AAA AAC TGT GAT ATG GAA TGC AAA GCG AAG AAC CAA GGA     144
Gly Glu Asn Lys Asn Cys Asp Met Glu Cys Lys Ala Lys Asn Gln Gly
 20              25                  30                  35

GGT AGT TAC GGC TAT TGC TAC AAG CTT GCA TGC TGG TGC GAA GGT TTG     192
Gly Ser Tyr Gly Tyr Cys Tyr Lys Leu Ala Cys Trp Cys Glu Gly Leu
             40                  45                  50

CCC GAA AGT ACA CCG ACT TAT CCC ATT CCT GGT AAA ACA TGC AGA ACA     240
Pro Glu Ser Thr Pro Thr Tyr Pro Ile Pro Gly Lys Thr Cys Arg Thr
                 55                  60                  65

AAA TAATGGCAAC ATCTTTTTAT TGTCACACAA CAGAAATATT GTAACGCTTC TTAATTGC 301
Lys
```

(2) INFORMATION FOR SEQ ID NO:4:

(i) SEQUENCE CHARACTERISTICS:
        (A) LENGTH: 81 amino acids
        (B) TYPE: amino acid
        (D) TOPOLOGY: linear (ii) MOLECULE TYPE: protein (xi) SEQUENCE DESCRIPTION: SEQ ID NO:4:

```
Ile Thr Ala Cys Leu Val Leu Ile Gly Thr Val Cys Ala Lys Glu Gly
-13         -10              -5                   1

Tyr Leu Val Asn Lys Ser Thr Gly Cys Lys Tyr Asn Cys Leu Ile Leu
        5               10                  15

Gly Glu Asn Lys Asn Cys Asp Met Glu Cys Lys Ala Lys Asn Gln Gly
 20              25                  30                  35

Gly Ser Tyr Gly Tyr Cys Tyr Lys Leu Ala Cys Trp Cys Glu Gly Leu
             40                  45                  50

Pro Glu Ser Thr Pro Thr Tyr Pro Ile Pro Gly Lys Thr Cys Arg Thr
                 55                  60                  65

Lys
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GAYGGNTGYA ARTYGGNTG                                                  19

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:6:

```
GGTGGCGACG ACTCCTGGAG CCCG                                      24
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:7:

```
TTGACACCAG ACCAACTGGT AATG                                      24
```

(2) INFORMATION FOR SEQ ID NO:8:

(i) SEQUENCE CHARACTERISTICS:
        (A) LENGTH: 345 base pairs
        (B) TYPE: nucleic acid
        (C) STRANDEDNESS: single
        (D) TOPOLOGY: linear     (ii) MOLECULE TYPE: DNA (genomic)

(ix) FEATURE:
        (A) NAME/KEY: CDS
        (B) LOCATION: 1..243

(ix) FEATURE:
        (A) NAME/KEY: sig_peptide
        (B) LOCATION: 1..39

(ix) FEATURE:
        (A) NAME/KEY: mat_peptide
        (B) LOCATION: 40..243

(xi) SEQUENCE DESCRIPTION: SEQ ID NO:8:

```
ATC ACT GCT TGT TTG GTC CTG ATC GGA ACA GTG TGC GCA AAG GAA GGT     48
Ile Thr Ala Cys Leu Val Leu Ile Gly Thr Val Cys Ala Lys Glu Gly
-13         -10                 -5                  1

TAT CTG GTG AAC AAG AGC ACA GGC TGT AAA TAC AAC TGC TTG ATA TTG     96
Tyr Leu Val Asn Lys Ser Thr Gly Cys Lys Tyr Asn Cys Leu Ile Leu
        5                   10                  15

GGA GAA AAC AAA AAC TGT GAT ATG GAA TGC AAA GCG AAG AAC CAA GGA    144
Gly Glu Asn Lys Asn Cys Asp Met Glu Cys Lys Ala Lys Asn Gln Gly
20                  25                  30                  35

GGT AGT TAC GGC TAT TGC TAC AAG CTT GCA TGC TGG TGC GAA GGT TTG    192
Gly Ser Tyr Gly Tyr Cys Tyr Lys Leu Ala Cys Trp Cys Glu Gly Leu
            40                  45                  50

CCC GAA AGT ACA CCG ACT TAT CCC ATT CCT GGT AAA ACA TGC CGA ACA    240
Pro Glu Ser Thr Pro Thr Tyr Pro Ile Pro Gly Lys Thr Cys Arg Thr
                55                  60                  65

AAA TAATGGCAAC ATCTTTTTAT TGTCACACAA CAGAAATATT GTAACGCTTC         293
Lys

TTAATTGCAA TTAAACAAAA TAAAATGTAA TACCTTCAAA AAAAAAAAA AA           345
```

-continued (2) INFORMATION FOR SEQ ID NO:9:

(i) SEQUENCE CHARACTERISTICS:
      (A) LENGTH: 81 amino acids
      (B) TYPE: amino acid
      (D) TOPOLOGY: linear (ii) MOLECULE TYPE: protein (xi) SEQUENCE DESCRIPTION: SEQ ID NO:9:

```
Ile Thr Ala Cys Leu Val Leu Ile Gly Thr Val Cys Ala Lys Glu Gly
-13          -10              -5                    1

Tyr Leu Val Asn Lys Ser Thr Gly Cys Lys Tyr Asn Cys Leu Ile Leu
     5               10              15

Gly Glu Asn Lys Asn Cys Asp Met Glu Cys Lys Ala Lys Asn Gln Gly
 20              25              30                       35

Gly Ser Tyr Gly Tyr Cys Tyr Lys Leu Ala Cys Trp Cys Glu Gly Leu
             40              45                   50

Pro Glu Ser Thr Pro Thr Tyr Pro Ile Pro Gly Lys Thr Cys Arg Thr
             55              60              65

Lys
```

PRIMARY SEQUENCE AND CDNA OF INSECTICIDALLY EFFECTIVE TOXINS FROM SCORPIONS OF THE GENUS CENTRUROIDES

CROSS REFERENCE TO RELATED APPLICATIONS

This application is a continuation-in-part of patent application Ser. No. 08/848,261 filed Apr. 29, 1997 now abandoned which claims a right to priority under 35 U.S.C. §119(e) based on Provisional Patent Application No. 60/017,007 filed Apr. 30, 1996, the contents of both of which are incorporated herein by reference.

FIELD OF THE INVENTION

The present invention relates to the general field of insecticidally effective peptides that can be used as bioinsecticides for pest control, in particular to insecticidally effective toxins isolated from the venom of Mexican scorpions of the genus Centruroides.

BACKGROUND OF THE INVENTION

Insect pests have detrimental effects on both agriculture and environment. Therefore, there has always been a need for new effective insecticides. Conventional synthetic insecticides widely used for several decades are toxic to a relatively broad spectrum of insects and may have negative consequences for the environment like groundwater contamination, toxicity to non-target organisms and potential human health-hazards caused by acute or chronic exposure. Consenquently, researchers continuously search for new more specific and environmentally non-hazardous insecticidal agents.

A natural microbial source of the insecticidal peptide delta endotoxin is the soil-dwelling bacterium *Bacillus thuringiensis* (B.t.) that is used to control pests of leaf-eating caterpillars, beetles and mosquitos (Priest, 1992; Aronson, 1993). There exist various studies dealing with the improvement of the insecticidal properties of B.t., e.g. the development of hybride bacterial cells containing the genes of the delta-endotoxins of B.t. *kurstaki* and B.t. *tenebrionis* (U.S. Pat. No. 4,797,279 Karamata et al., 1989) and the expression of a hybrid delta-endotoxin gene comprising parts of two variants of B.t. *kurstaki* (European Patent 0325400, 1989). Baculoviruses are major insect pathogens that exhibit a potential for insect control (Huber, 1986). Furthermore, they have been used in several studies as a vector to express an exogenous gene whose product is specifically toxic to insects, e.g. juvenile hormone esterase of *Heliothis virescens* (Hammock et al., 1990) as well as insecticidally effective toxins from the spider *Tegenaria agrestis* (Krapcho et al., 1995), from female mites of the species *Pyemotes tritici* (Tomalski and Miller, 1991) and from the scorpion *Androctonus australis* (Medea et al., 1991; Stewart et al., 1991).

The insect-specific toxins from arthropods like spiders, mites, scorpions or centipedes or predator insects like wasps as well as other insecticidally effective agents can also be applied introducing them directly to the target to be protected. The first examples of the expression of natural biological insecticides in transgenic plants were the expression of delta endotoxin from *Bacillus thuringiensis* (Barton et al., 1987) and of a cowpea trypsin inhibitor (Hilder et al., 1987) both in tobacco. Later, Barton et al. (U.S. Pat. No. 5,177,308, 1993) patented the development of transgenic plants which express an insect-specific toxin from the scorpions *Antroctonus australis* and *Buthus eupeus*. The expression of spider insecticides in transgenic plants and insect virus was patented in World-patent 9315108 (1993) and U.S. Pat. No. 5,441,934 (1995).

As mentioned above scorpions are natural sources of insecticidally effective peptides. Their venom contains a cocktail of various toxins (Possani, 1984) that serve to immobilize its insect prey as well as a defense against possible scorpion predators. The individual toxins display a certain specificity towards mammals, insects or crustaceans. Several toxins have been isolated that show activity in several species (De Lima et al., 1986; Eitan et al., 1990; Loret et al., 1991). The use of these toxins although effective as insecticides is not advisable because of possible side effects on domestic or other animals and humans. Scorpion toxins are required that are highly specific for insects and do not display toxic effects in mammals. Several of these have been described in the literature (Babin et al., 1976; Darbon et al., 1982; Lester et al., 1982; Kopeyan et al., 1990; Loret et al., 1990; Zlotkin et al., 1991). The Canadian patent 2,005,658 (1990) discloses an insecticidally effective peptide of the scorpion *Leirus quinquestriatus hebraeus.* The European patent 374753 (1990) reports insect-selective toxins of the scorpion *Androctonus australis, Leiurus quinquestriatus quinquestriatus, Buthotus judaicus, Leirus quinquestriatus hebraeus* and *Scorpiomaurus palmatus* as well as their expression in transgenic plants and microorganisms. Nevertheless, because of the need of specific and potent insecticides there is still a necessity to search and characterize new natural insecticidally effective toxins.

SUMMARY OF THE INVENTION

There is provided by this invention the amino acid sequences of novel toxins from scorpions of the genus Centruroides which are effective in insects but non-toxic to mammals. These basic polypeptides comprise about 60 to 70 amino acids, they contain eight cysteine residues at equivalent positions and show a similarity of 59%. Further provided by this invention is a novel cDNA sequence coding for one of the toxins of this invention.

DESCRIPTION OF THE DRAWINGS

FIG. 1 Primary structure of toxins Cn10 and CII3 The sequences were aligned according to the equivalent position of the cysteines. Similar residues of the two toxins are connected by vertical lines.

FIG. 2 cDNA sequence of toxin Cn10 and its deduced amino acid sequence The signal peptide is underlined, the polyadenylation site is printed in bold letters.

FIG. 3 Reverse-phase chromatography (HPLC) as the third step of the chromatographic purification of Cn10 Freeze-dried material of fraction II-5 (2.2 mg) from the second purification step was purified by HPLC on a semi-preparative $C_4$ reverse-phase column (25 cm×1 cm I.D., particle size 10 $\mu$m, Vydac, Hysperia, U.S.A.) eluted for 60 min with a linear gradient generated by mixing solution A (0.12% trifluoroacetic acid in water) and solution B (acetonitrile with 0.1% trifluoroacetic acid) at a flow rate of 2 ml/min. Peak number 3 represents Cn10.

FIG. 4 Reverse-phase chromatography (HPLC) as the third step of the chromatographic purification of CII3 Freeze-dried material of fraction II-5 (0.5 mg) from the second purification step was purified by HPLC on a semi-preparative $C_4$ reverse-phase column (25 cm×1 cm I.D., particle size 10 $\mu$m, Vydac, Hysperia, U.S.A.) eluted for 60 min with a linear gradient generated by mixing solution A (0.12% trifluoroacetic acid in water) and solution B (acetonitrile with 0.1% trifluoroacetic acid) at a flow rate of 2 ml/min. Peak number 3 corresponds to CII3.

DETAILED DESCRIPTION OF THE INVENTION

A. The Isolation of the Peptides From the Venom of Scorpions of the Genus Centruroides The source of the peptides of this invention may be the venom of any scorpion belonging to genus Centruroides. The venom of a scorpion can be obtained by electrical or manual stimulation of the telsons. Another method consists in the homogenization of the venom glands, presenting the disadvantage that the resulting preparation will be contaminated with high-molecular-weight compounds. The obtained dried venom is usually re-suspended in water and centrifuged to remove cellular debris and mucous material. Pure peptides can be obtained from the venom by applying various chromatographic methods, based on size-exclusion, ion-exchange and/or reverse-phase chromatography. These may be applied using conventional techniques, fast-performance liquid chromatography (FPLC) and/or high performance liquid chromatography (HPLC). The amino acid sequence of the purified toxins can be determined applying automated Edman degradation, amino acid analysis and other techniques known to those in the art.

More specifically, two insecticidally effective toxins have been isolated and characterized herein. They were purified to homogeneity from the venoms of the scorpions *Centruroides noxius* Hoffmann and *Centruroides limpidus limpidus* Karsch by applying three consecutive purification steps, size-exclusion, cation-exchange and reverse-phase chromatography. In the following the process of purification for both toxins will be explained in general terms, for detailed description of each purification step refer to the examples.

The scorpion venom was obtained by electrical stimulation of the anaesthetized animals. The released venom was then resuspended in water and centrifuged at 10,000×g for 15 min to remove cellular debris and mucous material. The soluble venom was lyophilized and kept at −20° C. until use.

The crude venom was thawed, dissolved in ammonium acetate buffer (20 mM, pH 4.7) and fractionated by size exclusion chromatography on a Sephadex G-50 column. The purification was followed by measuring the optical density at 280 nm. Fractions of 5 ml were collected, pooled and tested for toxicity.

As the next step in the purification scheme ion-exchange chromatography was performed using a carboxymethyl-cellulose column. Fractions of 2.5 ml were collected. The purification was followed by measuring the optical density at 280 nm. The pooled fractions were tested for toxicity.

Finally, high-performance liquid chromatography (HPLC) was done on a semi-preparative $C_4$ reverse-phase column eluted with a linear gradient generated by mixing solution A (0.12% trifluoroacetic acid in water) and solution B (acetonitrile with 0.1% trifluoroacetic acid). The flow rate was 2 ml/min. The purification was followed by measuring the optical density at 230 nm. Single peaks were collected and tested for toxicity.

The toxicity tests were conducted as explained under B.

Figure 1:
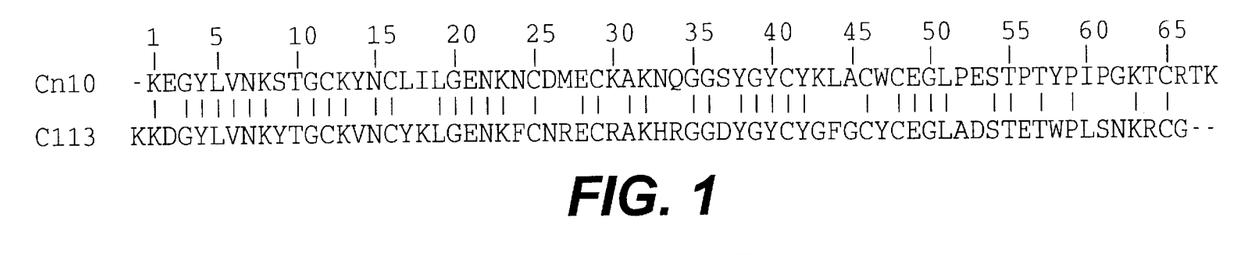
Figure 2:
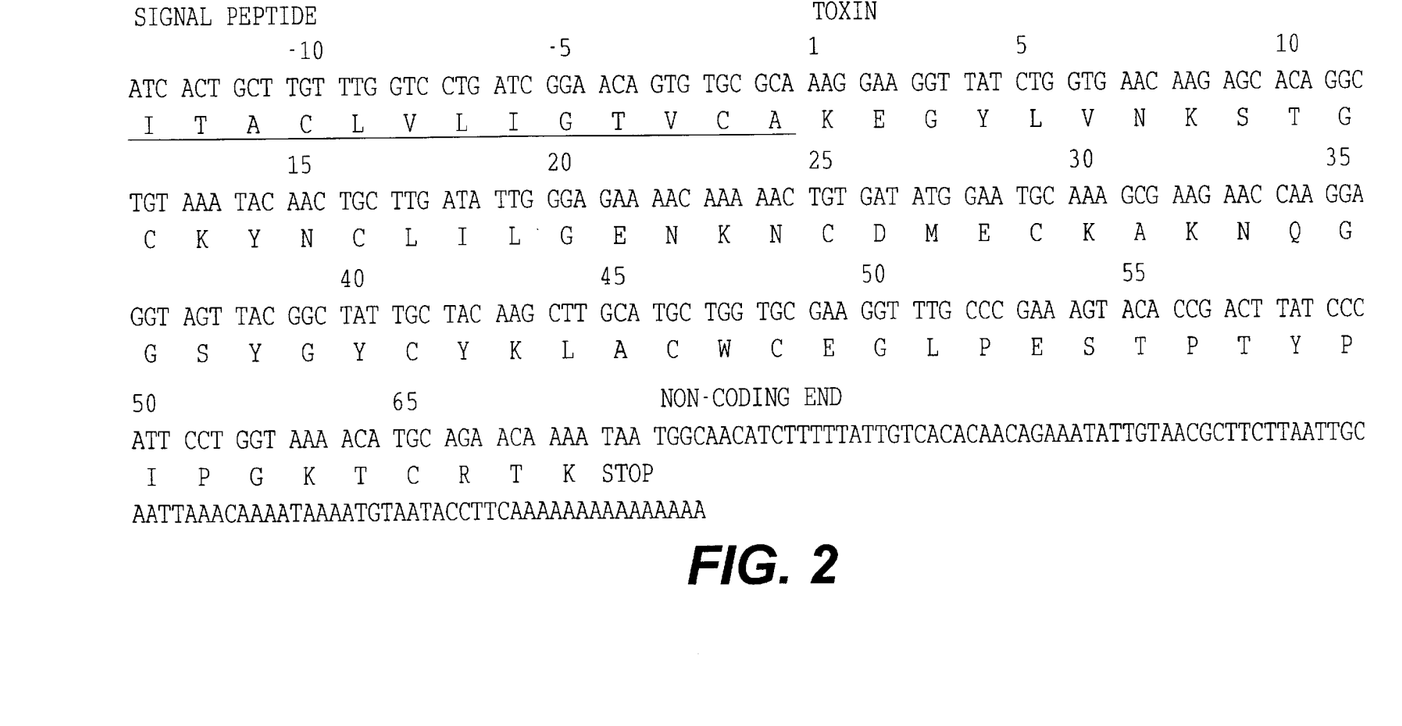

The sequence determination of the purified toxins which showed insecticidal activity was done by Edman degradation and amino acid analysis. The primary sequences of the toxins are shown in FIG. 1. The molecular mass of the two toxins named Cn10 and CII3 was calculated to be 7546 Dalton and 7620 Dalton, respectively. Scorpion toxins are often amidated at the carboxy-terminus, the amidation is the result of the processing of a longer precursor peptide which contains a glycine following the last amino acid in the mature peptide (Creighton T. E. (1993) Proteins: Structure and Molecular Properties. W. H. Freeman, New York, p.90). The cDNA encoding toxin Cn10 ends with a triplet coding for a lysine at amino acid position 68 (see FIG. 2). This amino acid is also present in the mature peptide which therefore is not expected to be amidated. In the case of CII3 the cDNA is not known. Gly67 is the last amino acid of the mature peptide which may be amidated.

It is expected that additional insecticidally effective peptides exist that may be isolated from the venom of the scorpions *Centruroides noxius* Hoffmann and *Centruroides limpidus limpidus* Karsch as well as from other scorpions of the genus Centruroides. Members of this family of toxins will fall within the scope of this invention if they share the following characteristics:

a) a size of approximately 60 to 70 amino acids corresponding to a molecular mass of approximately 7000 to 8000 Dalton, b) the presence of eight cysteine residues in positions equivalent to positions 12, 16, 25, 29, 41, 46, 48 and 65 in peptide Cn10, c) an isoelectric point above 7.0 (basic peptides), d) at least 59% similarity when aligned at the positions of the eight cysteines.

Moreover, minor modifications introduced by site-directed mutagenesis, amino acid substitution during solid phase synthesis or accidental mutations in hosts that can be used to produce the peptides of this invention may result in peptides which show similar or enhanced activity compared to the peptides of this invention. All these modifications are included in the invention as long as the insecticidal activity is preserved. A "mutation" in a peptide alters its primary structure by deletion, substitution or addition of single amino acids due to changes in the DNA sequence which codes for it. A "deletion" represents a primary sequence with one or more amino acids missing in comparison to the wild-type peptide sequence. An "addition" contains one or more additional amino acids compared to the wild type. A "substitution" results from the replacement of single amino acid residues by others. Furthermore, it is understood that peptides resulting from modifications like amidation of carboxyl groups or other chemical modifications of functional groups of amino acid residues within the peptide will be included in the invention as long as any insecticidal activity is retained.

B. Biological Tests

The venom fractions from each purification step and the purified toxins can be assayed for their insecticidal activity in various test animals. The assay can be done by direct injection of the purified toxins into the test-animal, by feeding or other methods. Furthermore, biological tests in mammals are usually done to test for possible side-effects on humans.

More specifically, the biological activity of the venom fractions and purified toxins was determined by injecting the material in mammals (mice) and insects (crickets Achaeta spp.) and by feeding assays in larvae of western corn rootworms (WCR, *Diabrotica virgifera virgifera* LeConte). It was detected if a certain quantity of toxin per average body weight of test animal was "non-toxic", "toxic" or "lethal". "Non-toxic" means the animals show no symptoms of intoxication within 24 hrs from the injection or feeding, similarly to having been given buffer or water alone. "Toxic" means that they show symptoms of intoxication like excitability, salivation, lacrimation, dyspnea, temporary paralysis of limbs in case of mice or paralysis in case of crickets as well as larvae of WCR. The toxic effect will be assigned as "lethal" when one of the test animals died of intoxication.

Adult albino mice (average weight 20 g) of the strain CD 1 were injected intraperitoneally with a given quantity (see examples) dissolved in 200 μl PBS buffer. Crickets (average body weight 0.5 g) were injected with toxic material dissolved in 20 μl bi-distilled water. Larvae of WCR (5 days old, average body weight 2 mg) were fed with a mixture of toxin, 2% green food coloring and 5% sucrose in 1 μl $H_2O$. The coloring was applied to check if the animal injested the toxin. To prove that the toxic effects were particularly due to the application of the toxic material control animals were injected with buffer or water alone.

It is understood that any peptide from scorpions of the genus Centruroides to which the above under A listed criteria apply and that shows insecticidal effect in any sort of insect test animal will fall within the scope of this invention.

C. Identification of the Coding Sequence of the Insecticidally Effective Peptide Cn10 of This Invention Further provided by this invention is the cDNA sequence coding for the toxin Cn10 from *Centruroides noxius* Hoffmann.

There are various methods of isolating the part of the genomic DNA of an organism that is responsible for the production of a particular peptide. One of these methods consists in the construction and screening of cDNA libraries with specific oligonucleotides (Sambrook J., Fritsch E. F. and Maniatis T. (1989) Molecular cloning, A laboratory manual. 2nd edition, Cold Spring Harbor Laboratory Press, volume 2, chapter 8). Briefly, oligonucleotides are synthesized on the basis of known amino acid or DNA sequences coding for peptides that show a high similarity to the peptide of interest. In case of synthetic DNA which was designed from a part of the primary sequence of a peptide "degenerate" probes, well known to those in the art, have to be used. The oligonucleotide may comprise the sequence designed or the complementary DNA strand to the part of the known sequence. Instead of synthetic DNA probes already isolated cDNA coding for highly similar peptides can also be used. The DNA probes should at least comprise 15 nucleotides to ensure efficient binding to complementary stretches of DNA in the library. The library of cDNA consists of a pool of cDNA molecules derived by reverse transcription from mRNAs isolated from the venom glands of scorpions. The cDNA is usually empackaged in any of the known bacteriophage vectors. In this stage the library can be stored indefinetely. Strains of bacterial cells are then infected by these bacteriophages that give rise to the formation of plaques. The plaques may be screened with the above described DNA probes. The isolated positive clones are usually amplified from the bacteriophages by Polymerase Chain Reaction (PCR) using adequate primers. The resultant product represents cDNA that may be subcloned into any of a number of known cloning vectors and transformed into bacterial cells. From there the DNA sequence is determined applying methods well known to those in the art.

More specifically, a cDNA library prepared from telsons of the scorpion *Centruroides noxius* Hoffmann packaged in the bacteriophage vector λctl1 was screened under conditions of high stringency using a truncated cDNA clone, Cngtl, of 132 nucleotides (Becerril et al., 1993). Cngtl codes for a truncated toxin of 44 amino acids; the first 41 amino acids are in 40 positions identical to the C-terminal stretch of the insecticidally effective toxin CsEv3 of *Centruroides sculpturatus* Ewing (Babin et al., 1974). In the second step of the screening a degenerated oligonucleotide was used which corresponds to amino acids 10 to 16 of the same toxin CsEv3. The search resulted in 13 positive clones one of which was subcloned into the phagemid pKS+ and the construction transformed into *E. coli* cells. The DNA of the insert was then sequenced applying the dideoxy-mediated chain-termination method. The cDNA of Cn10 comprises 346 nucleotides including the polyadenylation site (see FIG. 2). It codes for the mature peptide of 68 amino acids and a signal peptide comprising 13 amino acids. A comparison of the signal peptide with highly similar signal peptides of cDNAs of related toxins from *Centruroides noxius* Hoffmann (Becerril et al., 1993) showed that it may be truncated at amino acid -13. The complete signal peptide should consist of 18 to 21 amino acids.

In the venom of scorpions of the same genus there exist families of related toxins that have very similar amino acid sequences. Therefore, it is expected that the screening of cDNA libraries from scorpions of the genus Centruroides will result in various clones of related cDNAs. It is understood that these genes encoding peptides to which the above under A listed criteria apply are also within the scope of this invention as long as any insecticidal activity of the resulting peptides is retained.

D. Application of the Peptide as Insecticide

The insecticidally effective peptides of this invention can be used as insecticides for pest control. The specificity of the peptides towards certain insect pests will have to be evaluated by further biological tests. The peptides can be isolated from venom of the scorpions *Centruroides noxius* Hoffmann, *Centruroides limpidus limpidus* Karsch or other scorpions of the genus Centruroides. They can be produced by solid-phase peptide synthesis or as recombinant peptides. The peptides can be applied directly by contacting the pests with an effective amount of the peptide or agriculturally or horticulturally acceptable salts thereof.

Alternatively, it can be produced in expression vectors like baculovirus or *bacillus thuringiensis* as well as in transgenic plants. The various methods of controlling insect pest using the peptides of this invention can be used in combination with other control methods.

EXAMPLES

The following examples are given to illustrate particular compositions and methods within the scope of the present invention but they are not intended to limit the scope of the present invention.

General Methods

Under this point methods used for purification and sequencing of the peptides of this invention are described in general, the details for the processing of each peptide are given in the examples.

1. Purification Process

The scorpion venom was obtained by electrical stimulation of the anaesthetized animals. The released venom was then resuspended in - water and centrifuged at 10,000×g for 15 min to remove cellular debris and mucous material. The soluble venom was lyophilized and kept at −20° C. until use.

Size exclusion chromatography was carried out on a Sephadex G-50 column (medium grade, Pharmacia Fine Chemicals, Uppsala, Sweden, bed volume 200 cm×2 cm I.D.) using ammonium acetate buffer (20 mM, pH 4.7) for equilibration and as elution buffer. The flow rate was 15 ml/h. The purification was followed by measuring the optical density at 280 nm using a spectrometer DU-50 (Beckman Instruments, Fullerton, U.S.A.). Fractions of 5 ml were collected using a 2070 Ultrarac II fraction collector (LKB Bromma, Sweden), pooled and tested for toxicity.

Ion-exchange chromatography was performed using a carboxymethyl-cellulose column (CM-32, Whatman Inc., Clifton, U.S.A., bed volume 30 cm×0.9 cm I.D.) using as elution buffer 20 mM ammonium acetate, pH 4.7 with a linear gradient of NaCl (250 ml 0 M–250 ml 0.5 M). The flow rate applied was 30 ml/h. Fractions of 2.5 ml were collected using a 2070 Ultraracil fraction collector (LKB Bromma, Sweden). The purification was followed by measuring the optical density at 280 nm using a spectrometer DU-50 (Beckman Instruments, Fullerton, U.S.A.). The pooled fractions were tested for toxicity.

High-performance liquid chromatography (HPLC) was done with a Waters HPLC system (Waters 600E System controller and Waters 745B data module, Millipore, Milford, U.S.A.) on a semi-preparative $C_4$ reverse-phase column (25 cm×1 cm I.D., particle size 10 µm, Vydac, Hysperia, U.S.A.) eluted with a linear gradient generated by mixing solution A (0.12% trifluoroacetic acid in water) and solution B (acetonitrile with 0.1% trifluoroacetic acid). The flow rate was 2 ml/min. The purification was followed by measuring the optical density at 230 nm using a Water Lambda-Max LC spectrometer model 481 (Millipore, Milford, U.S.A.). Single peaks were collected and tested for toxicity.

2. Sequence Determination

For sequence determination the purified toxins were reduced and carboxy methylated as follows. The freeze-dried toxin (200 µg) was dissolved in 200 µl Tris HCl buffer, pH 8.6, containing 6 M guanidinium hydrochloride and 1 mg/ml EDTA. 0.5 mg dithiothreitol was added and the mixture treated with $N_2$ for 5 min and then incubated for 45 min at 55° C. 7 mg iodoacetic acid was added and the mixture incubated for 30 min at room temperature. The reaction mixture was purified on a Biogel P-30 column (30 cm×0.9 cm I.D., Bio-Rad Hercules, U.S.A.) using 20% (v/v) acetic acid as eluent. The purified reduced and carboxy methylated toxin was then digested by the endoproteases V8 (Boehringer, Mannheim, Germany) in 100 mM ammonium bicarbonate and ASP-N (Boehringer, Mannheim, Germany) in 50 mM sodium phosphate buffer, ph 8.0 using in both cases a ratio of 200 µg:2 µg of toxin : endoprotease. The resulting peptide mixture were purified on a analytic $C_{18}$ reverse phase column (25 cm×0.46 I.D., particle size 5 µm, Vydac, Hyspheria, U.S.A.) eluted with a linear gradient generated by mixing solution A (0.12% trifluoroacetic acid in water) and solution B (acetonitrile with 0.1% trifluoroacetic acid). The flow rate was 1 ml/min. Single peaks were collected manually. N-terminal amino acid sequence analysis was done by Edman degradation using a microsequencer model 6400/6600 (MilliGen/Biosearch, Burlington, U.S.A.).

Specific Examples

Example 1

Initial Fractionation of the Crude Venom of Centruroides noxius Hoffmann

The first step of the purification of the venom of Centruroides noxius Hoffmann was size exclusion chromatography. 345 mg venom was thawed, dissolved in 5 ml ammonium acetate buffer (20 mM, pH 4.7) and purified on a Sephadex G-50 as described in General Methods. Three fractions were obtained. The second fraction represents the toxic peptides of the venom. It contained 63% of the material recovered. The material was lyophilized and kept at −20° C.

Example 2

Further Purification of Fraction II of Centruroides noxius Venom

Two hundred fifty seven mg freeze-dried material representing peak II of two independent chromatographic runs of the first purification step were dissolved in 15 ml ammonium acetate buffer (20 mM, pH 4.7) and then further purified by ion-exchange chromatography as outlined in General Methods. 14 fractions were obtained and tested for toxicity. Adult albino mice (average weight 20 g weight) of the strain CD 1 were injected intraperitoneally with 20 µg of protein dissolved in 200 µl PBS buffer. Crickets (average body weight 0.5 g) were injected with 20 µg material dissolved in 20 µl bi-distilled water. Fractions 2, 3, 4, 5 and 7 were shown to be non-toxic to mice at the applied concentration. Fractions 5, 7, 8, 9 and 10 were tested to be toxic to insects.

Example 3

Further Purification of Fraction II.5 of Centruroides noxius Venom

Figure 3:
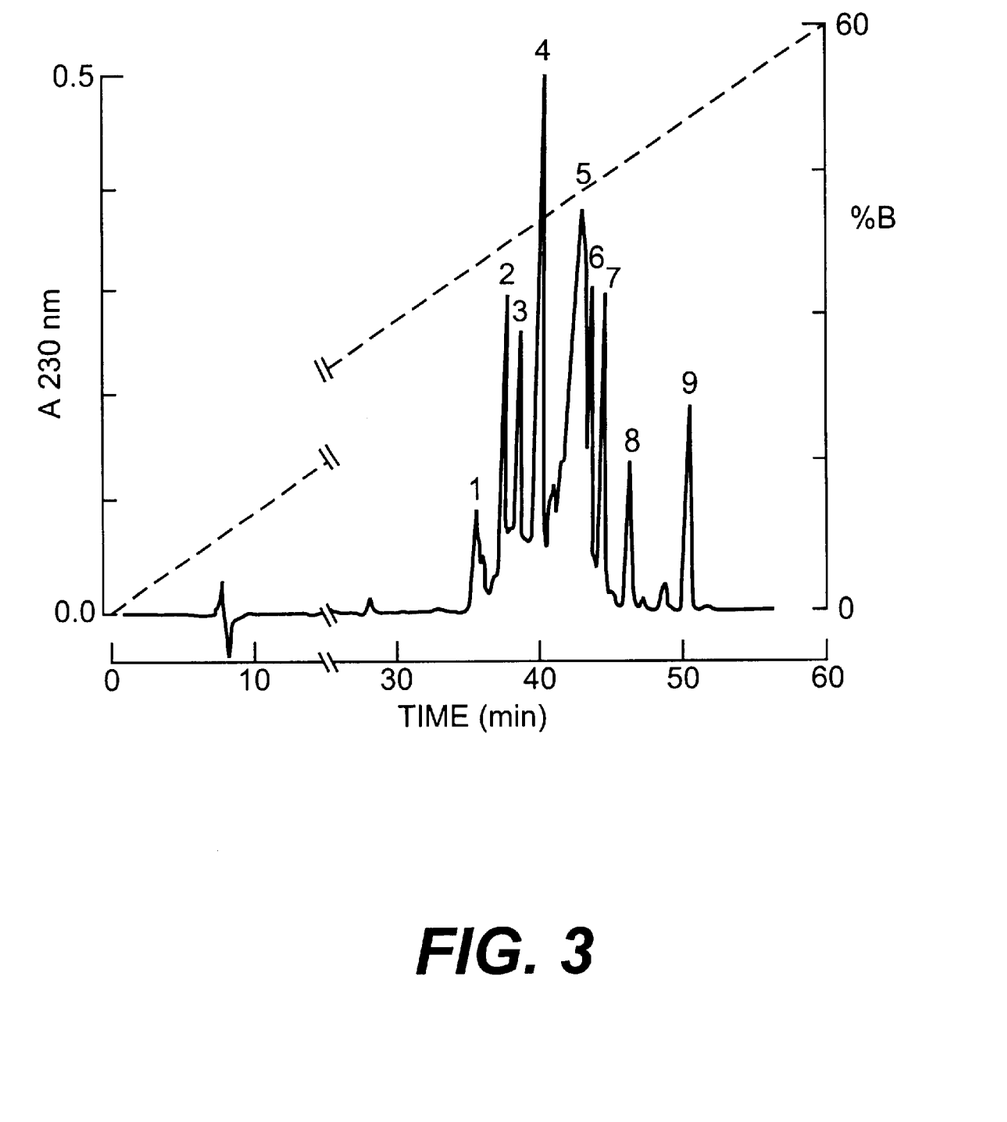

Two point two mg freeze-dried material of peak 5 from the second purification step of Centruroides noxius Hoffmann venom was further purified by high-performance liquid chromatography as outlined in General Methods. Nine peaks were obtained (see FIG. 3). Toxin Cn10 eluted as a single peak (number 3) at a retention time of 37.44 min.

The insecticidal effect of toxin Cn10 was tested by injection in crickets (Achaeta spp.). Various doses of Cn10 were applied from 10 µg per animal (average body weight 0.5 g) up to 50 µg. The onset of toxicity was observed at a dose of 15 µg per animal whereas the onset of a lethal effect at a dose of 50 µg where two out of four crickets died within six hours. Furthermore, it was proved that Cn10 is not toxic to mice injecting up to 500 µg/20 g average body weight intraperitoneally.

The sequence of Cn10 (see FIG. 1) was determined as outlined in General Methods.

Example 4

Initial Fractionation of the Crude Venom of Centruroides limpidus limpidus Karsch The first step of the purification of the venom of Centruroides limpidus limpidus Karsch was size exclusion chromatography. 340 mg venom were thawed, dissolved in 6 ml ammonium acetate buffer (20 mM, pH 4.7) and purified on a Sephadex G-50 as described in General Methods. Four fractions were obtained. The second fraction containing the toxic peptides of the venom of Centruroides limpidus limpidus represented 77.5% of the material recovered. The material was lyophilized and kept at −20° C.

Example 5

Further Purification of Fraction II of Centruroides limpidus limpidus Karsch Venom Ninety seven mg freeze-dried material representing peak II of the first purification step was dissolved in 5 ml ammonium acetate buffer (20 mM, pH 4.7) and then further purified by ion-exchange chromatography as outlined in General Methods. 12 fractions were obtained plus one additional fraction number 13 after eluting the column with 1 M of NaCl. Fraction 13 contained 3.1% of the material recovered. It was injected intraperitoneally into adult albino mice (average weight 20 g weight) of the strain CD 1 applying 150 µg protein dissolved in 200 µl PBS buffer. No toxic effect to mice was detected.

Example 6

Figure 4:
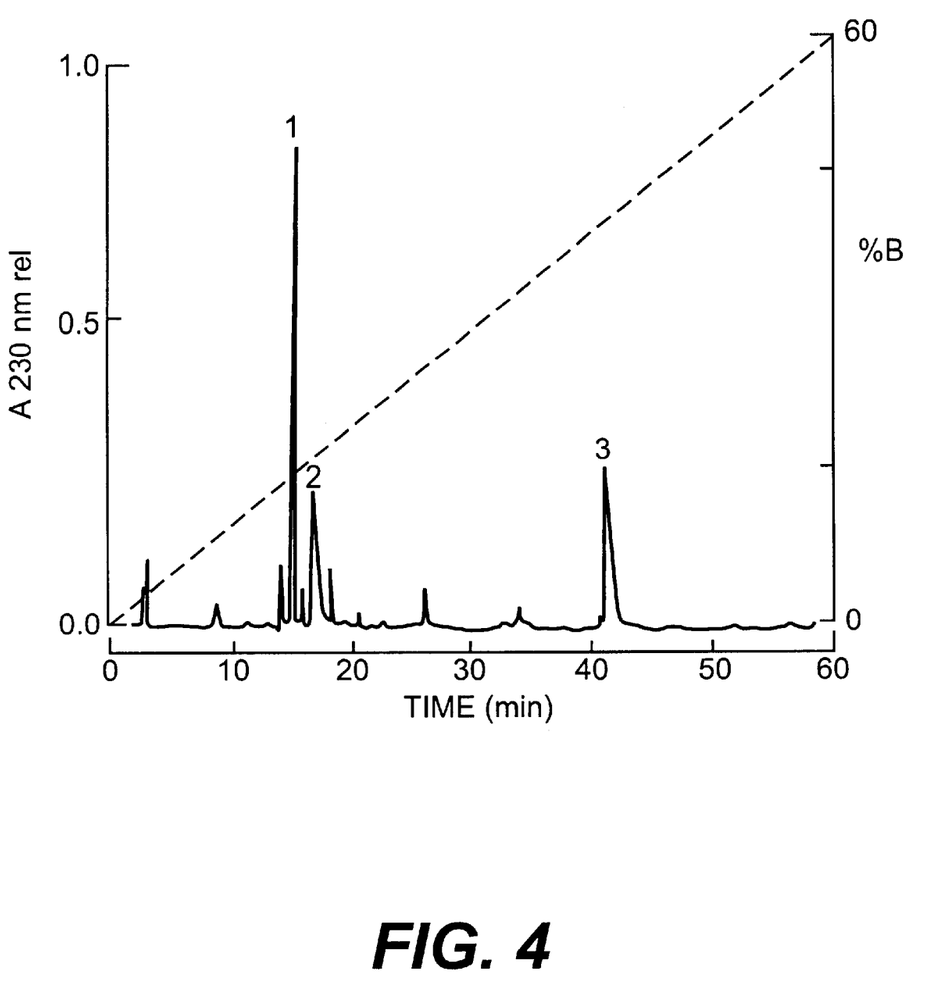

Further Purification of Fraction II.13 of Centruroides limpidus limpidus Karsch Venom Five hundred µg freeze-dried material of peak 13 from the second purification step of Centruroides limpidus limpidus Karsch venom was diluted in 50 μl of solution A and further purified by high-performance liquid chromatography as outlined in General Methods. Three peaks w re obtained (see FIG. 4). Toxin CII3 eluted as a single peak with a retention time of 41.5 min, it contained 40.8% of the recovered material. The insecticidal effect of CII3 was tested by feeding assays using larvae of the western corn rootworm (WCR, *Diabrotica virgifera virgifera* LeConte). Toxic effects were observed after application of 0.3 μg toxin per animal (average body weight 2 mg). Furthermore, it was proved that CII3 is not toxic to mice up to concentrations of 150 μg per animal. The sequence of CII3 (see FIG. 1) was determined as outlined in General Methods.

Example 7

Cloning of the cDNA Encoding Toxin Cn10

Around 2500 telsons of *Centruroides noxius* Hoffmann (around 6 g) were obtained, treated with liquid nitrogen and pulverized in a mortar. The following steps comprising the isolation of total RNA, the purification of poly(A)+RNA and the synthesis and construction of the cDNA library in λgt11 were performed according to the instructions supplied in the commercial kits utilized (RPN1264, RPN1511, RPN1256Y/Z, respectively, Amersham, Aylesbury, England). The screening of the library was carried out in two steps. In the first step approximately 14,000 plaques were analyzed under conditions of high stringency using a truncated cDNA clone, Cngtl, of 132 nucleotides (Becerril et al., 1993). Cngtl codes for a truncated toxin of 44 amino acids; the first 41 are in 40 identical to the C-terminal stretch of the arthropod-specific toxin CsEv3 of *Centruroides sculpturatus* Ewing. The clone was $^{32}$P-end-labeled by T4 polynucleotide kinase. Replica filters were prehybridized for 2–8 h at 42° C. in 6×SSC pH 7.6 containing 5×Denhardt's/0.1% SDS/100 μg per ml calf thymus sonicated and denatured DNA (cstd DNA)/0.05% sodium pyrophosphate/50% formamide. Filters were then hybridized in 6×SSC pH 7.6/1×Denhardt's/100 μg per ml ctsd DNA/0.05% sodium pyrophosphate/50% formamide/ $^{32}$P-end-labeled oligo probe for 12–16 h at 42° C. Successive washes were performed in 6×SSC pH 7.6/0.05% sodium pyrophosphate/0.1% SDS at 37° C. for 5 min and once at 42° C. for 5 min before autoradiography using X-AR film with intensifying screens for 18 h at −70° C. The isolated positive clones were amplified by overnight liquid cultures, the DNA purified and digested by restriction enzymes. The inserts were then purified electrophoretically, tranferred onto paper and tested with an oligo probe designed from amino acids 10–16 of toxin CsEv3 -(GAYGGNTGYA ARTYGGNTG) (SEQ ID NO:5). The oligo probe was synthesized in a DNA Synthesizer Model 381A from Applied Biosystems (Foster City, U.S.A.). The conditions of pre- and hybridization were the same as for the first step except that the incubations were performed at 37° C. and without formamide. 13 positive clones were isolated and stored in SM buffer at −4° C. One of these clones was amplified by PCR (GeneAmp PCR System Perkin Elmer, 30 rounds of temperature cycling: 92° C. for 1 min, 50° C. for 1 min, 72° C. for 3min followed by a final period of 10 min at 72° C.) using λgt11 forward primer (GGTGGCGACG ACTCCTGGAG CCCG) (SEQ ID NO:6) and λgt11 reverse primer and (TTGACACCAG ACCAACTGGT AATG) (SEQ ID NO:7) Vent$^R$ DNA-polymerase (BioLabs Beverly, U.S.A.). The PCR product was purified from the gel and subcloned into the EcoRV site of the phagemid Bluescript II KS+(Stratagene LaJolla, U.S.A.). Subsequently competent *E. coli* DH5-α cells (GIBCO BRL Gaithersburg, U.S.A.) were transformed. The plasmid DNA of white colonies with an insert of the expected size of around 400 bp was isolated and the inserts sequenced using the Sequenase kit T7 DNA polymerase (US Biochemical Cleveland, U.S.A.). The same αgt11 primers used for PCR were used for DNA sequencing.

What is claimed is:

1. An insecticidally effective peptide, named Cn10, purified from the venom of the scorpion *Centruroides noxius* Hoffmann, consisting of the amino acid sequence SEQ ID NO: 1 or functionally equivalent mutations having at least 85% identity with SEQ ID NO: 1.

2. The peptide according to claim 1, which is toxic to insects but non-toxic to mammals.

3. An insecticidally effective peptide, named C113, purified from the venom of the scorpion *Centruroides limpidus limpidus* Karsch, consisting of the amino acid sequence SEQ ID NO: 2 or functionally equivalent mutations having at least 80% identity with SEQ ID NO: 2.

4. The peptide according to claim 3, which is toxic to insects but non-toxic to mammals.

5. A peptide isolated and purified from the venom of scorpions of the genus Centruroides, consisting of a sequence of 60 to 70 amino acids, containing eight cysteine residues in equivalent positions to positions 12, 16, 25, 29, 46, 48, and 65 in the peptide of claim 1, being of basic character, showing at least 85% identity to Cn10 or at least 80% identity to C113 and being insecticidally effective.

6. A preparation which contains at least one insecticidally effective peptide according to any one of claims 1 to 5.

7. A method of controlling insect pests comprising the step of administering at least one insecticidally effective peptide according to any one of claims 1 to 5.

8. An insecticidally effective peptide purified from the venom of the scorpion *Centruroides noxius* Hoffmann, consisting of the amino acid sequence SEQ ID NO:1.

9. An insecticidally effective peptide purified from the venom of the scorpion *Centruroides limpidus limpidus* Karsch, consisting of the amino acid sequence SEQ ID NO: 2.

10. A preparation which contains at least one insecticidally effective peptide according to claim 8 or claim 9.

11. A method of controlling insect pests comprising the step of administering at least one insecticidally effective peptide according to claim 8 or claim 9.

* * * * *